US010345185B1

(12) United States Patent
Nguyen et al.

(10) Patent No.: US 10,345,185 B1
(45) Date of Patent: Jul. 9, 2019

(54) THERMAL LEAK DETECTOR

(71) Applicant: The United States of America as Represented by the Secretary of the Navy, Washington, DC (US)

(72) Inventors: Duy Nguyen, San Diego, CA (US); Sean A. Alexander, San Diego, CA (US); Timothy D. Wenzler, San Diego, CA (US); Wesley R. McGinn, San Diego, CA (US); Michael W. Godwin, San Diego, CA (US); Phillip M. Marquez, Lakeside, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 57 days.

(21) Appl. No.: 15/665,880

(22) Filed: Aug. 1, 2017

Related U.S. Application Data

(60) Provisional application No. 62/384,891, filed on Sep. 8, 2016.

(51) Int. Cl.
| | |
|---|---|
| *G01K 17/00* | (2006.01) |
| *G01M 3/00* | (2006.01) |
| *G01K 7/02* | (2006.01) |
| *G01N 25/72* | (2006.01) |

(52) U.S. Cl.
CPC ............... *G01M 3/002* (2013.01); *G01K 7/02* (2013.01); *G01N 25/72* (2013.01)

(58) Field of Classification Search
CPC .......... G01K 13/00; G01K 1/14; G01K 1/024; G01K 1/08; G01K 2201/00; G01K 2205/00; G01K 13/002; G01K 13/02; G01K 7/02; G01J 5/04
USPC ...................... 374/141, 163, 208, 179, 4, 29
See application file for complete search history.

(56) References Cited

U.S. PATENT DOCUMENTS

| | | | | |
|---|---|---|---|---|
| 3,091,235 A | * | 5/1963 | Richards | A61B 1/0051 600/142 |
| 3,938,544 A | * | 2/1976 | Bernaerts | F16K 5/00 374/5 |
| 2002/0196838 A1 | * | 12/2002 | Lee | G01K 1/14 374/155 |
| 2003/0159527 A1 | * | 8/2003 | Cardinale | G01M 3/20 73/864.35 |
| 2006/0076669 A1 | * | 4/2006 | Yu | G01K 13/002 257/698 |
| 2019/0101453 A1 | * | 4/2019 | Foreman, Jr. | G01K 1/08 |

FOREIGN PATENT DOCUMENTS

CN             203087318 U   *   7/2013

* cited by examiner

*Primary Examiner* — Gail Kaplan Verbitsky
(74) *Attorney, Agent, or Firm* — James M. Saunders

(57) ABSTRACT

Embodiments are directed to thermal leak detection. An apparatus according to the embodiments has a hollow probe having a proximal and a distal end. A hollow insulated handle is attached to the proximal end of the hollow probe. A measurement head is attached to the distal end of the hollow probe. An electronic thermometer is electrically-connected to the measurement head.

7 Claims, 7 Drawing Sheets

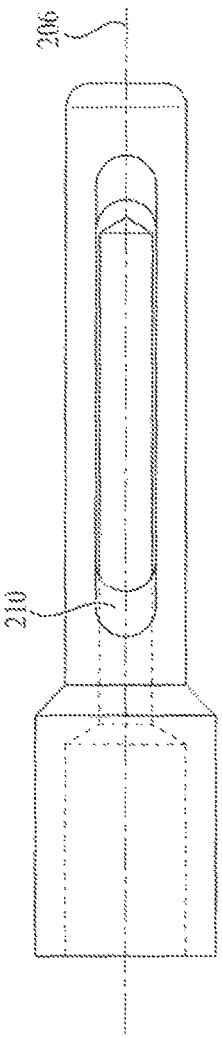
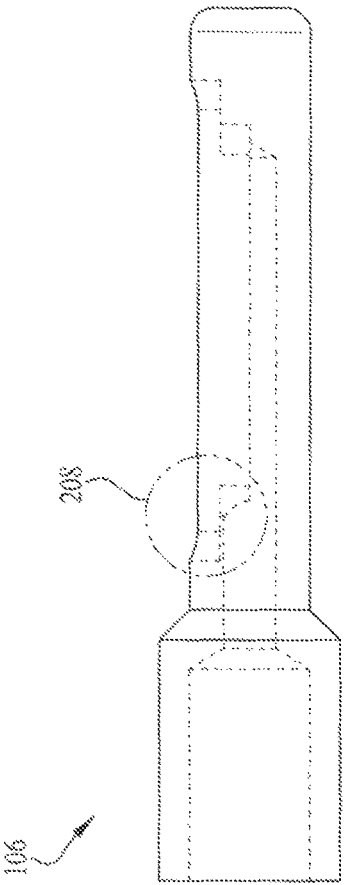
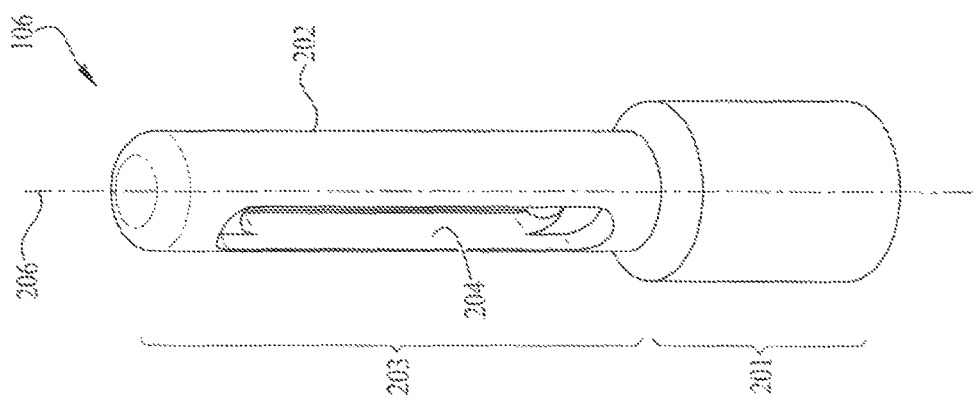
Fig. 2B
Fig. 2C
Fig. 2A

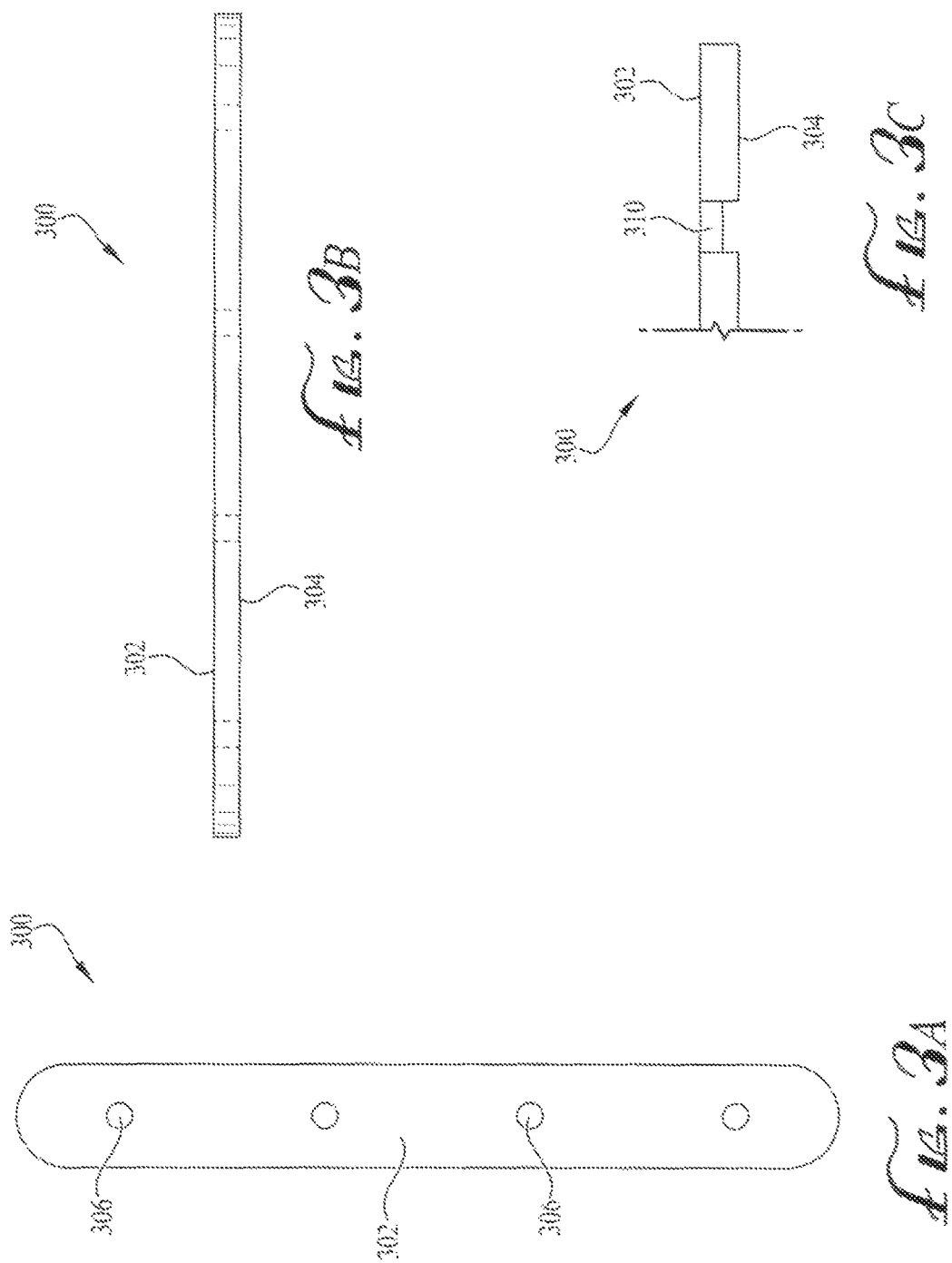

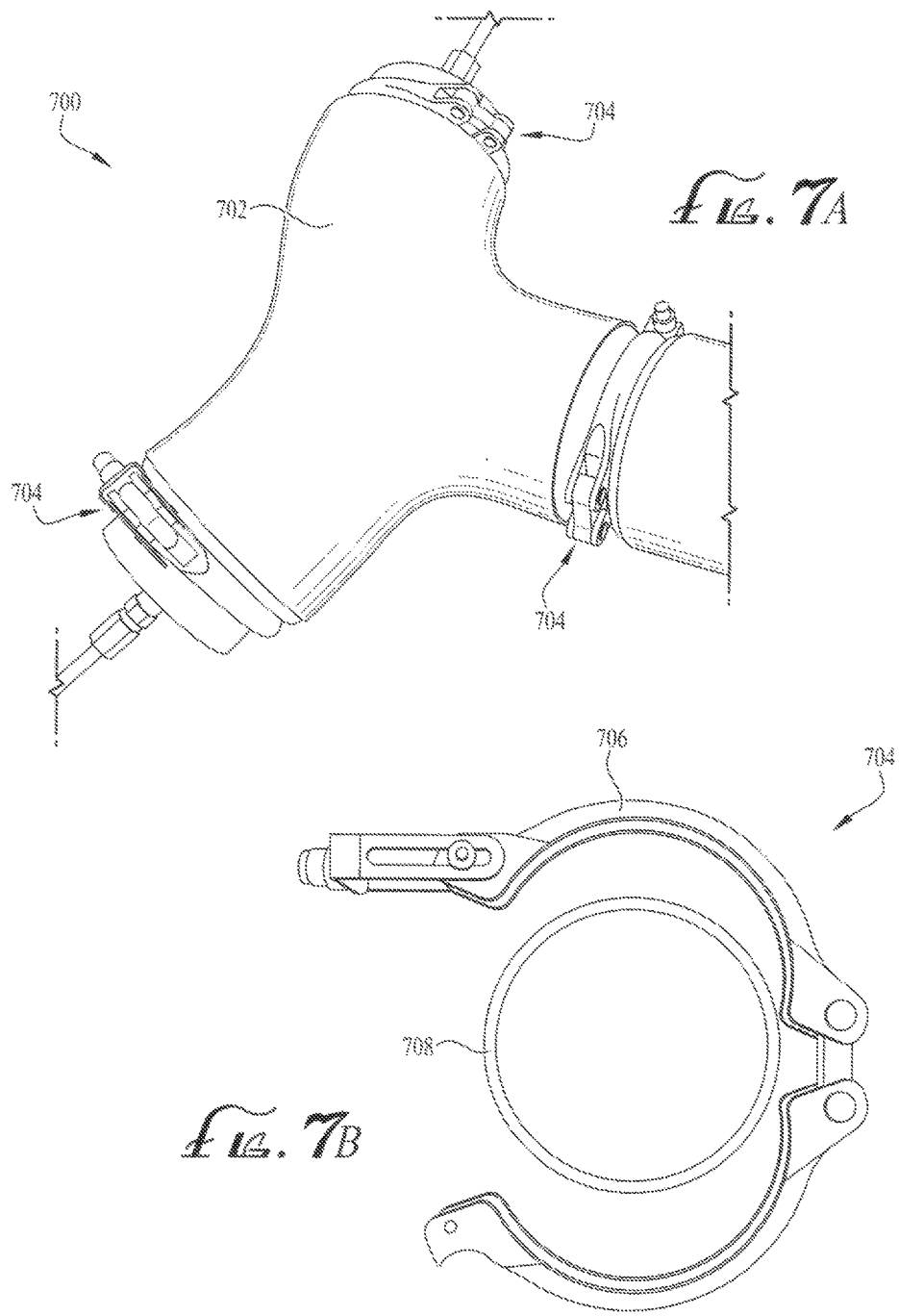

THERMAL LEAK DETECTOR

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD

The embodiments generally relate to thermal leak detection.

BRIEF DESCRIPTION OF THE DRAWINGS

FIG. 2A is a perspective view of a measurement head according to some embodiments.

FIG. 2B is a side view of the measurement head in FIG. 2A.

FIG. 2C is another side view depicting the internal configuration of the measurement head in FIG. 2A.

FIG. 3A is a plan view of a thermocouple plate according to some embodiments.

FIG. 3B is a side view of the thermocouple plate of FIG. 3A.

FIG. 3C is a partial side view depicting thermocouple orientation in the thermocouple plate of FIG. 3A.

FIG. 7A illustrates an exemplary wye duct from a pneumatic system that embodiments are configured to act upon.

FIG. 7B illustrates an exemplary V-band clamp and E-seal used with the wye duct in FIG. 7A.

Figure 1:
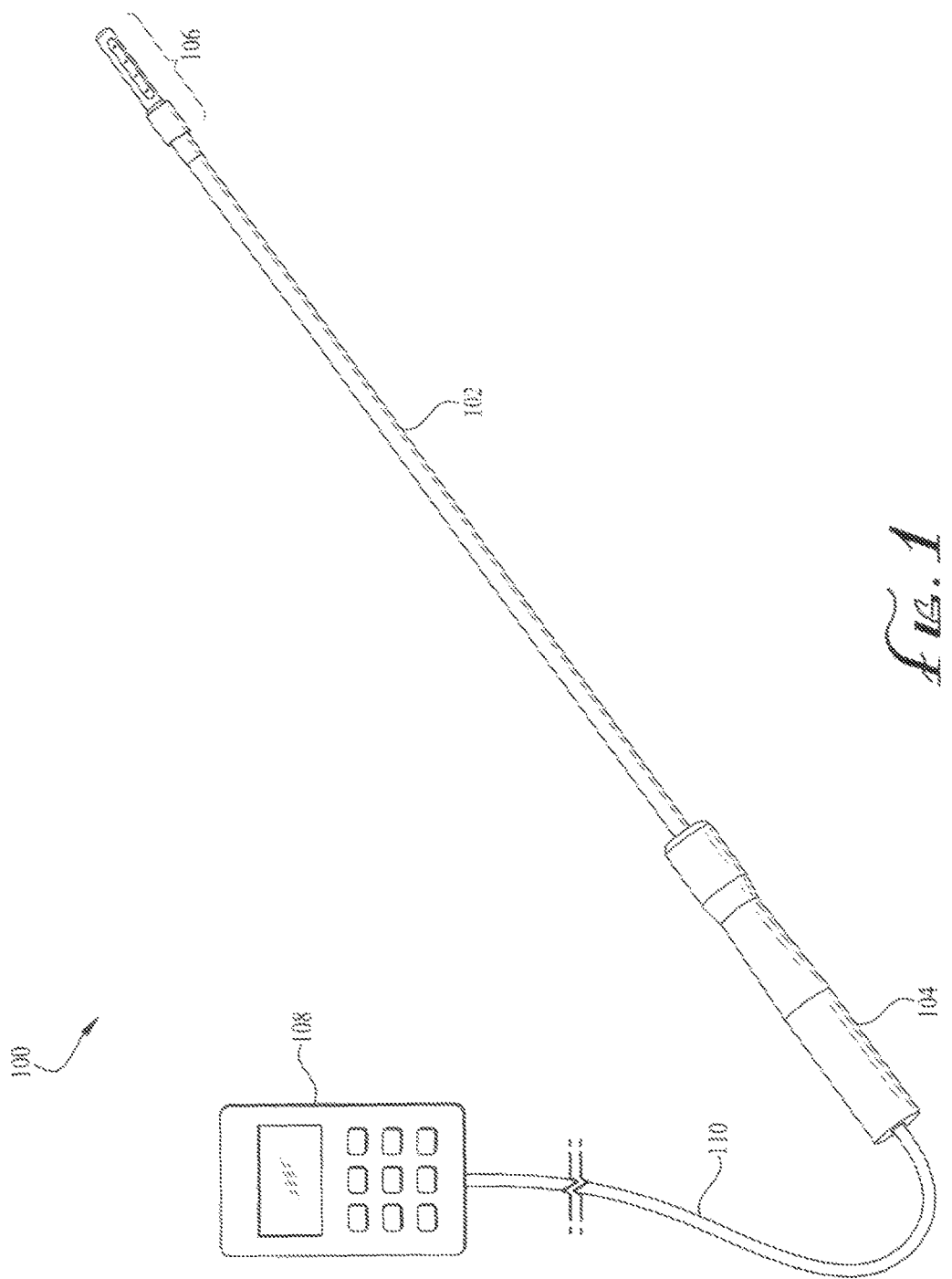
FIG. 1 is an isometric view of an apparatus depicted in a linear, straight-line orientation, according to some embodiments.

It is to be understood that the foregoing general description and the following detailed description are exemplary and explanatory only and are not to be viewed as being restrictive of the embodiments, as claimed. Further advantages of the embodiments will be apparent after a review of the following detailed description of the disclosed embodiments, which are illustrated schematically in the accompanying drawings and in the appended claims.

DETAILED DESCRIPTION OF EMBODIMENTS

Embodiments are directed to mitigating risk, improving worker safety, and supporting higher fleet readiness. Embodiments accomplish this by a more efficient leak detection apparatus. Lack of viable leak detection devices for aircraft has resulted in multiple Hazardous Reports (HAZREPs). In particular, fighter aircraft maintenance personnel have used their hands to feel for leaks around environmental control system (ECS) pneumatic ducting, where leak temperatures can range from about 20 degrees Fahrenheit (F) to about 500 degrees F. Pneumatic ducting systems with lower temperatures, such as at 20 degrees F., result in lower temperature changes (lower temperature delta) in aircraft bays as compared with higher temperature pneumatic ducting systems. Leaks in higher temperature pneumatic ducting systems, such as those about 200 degrees F. and above can result in substantial injuries to aircraft maintainers' exposed hands. The embodiments described herein are applicable to thermal leak detection from about 20 degrees F. to about 500 degrees F. In particular, however, the embodiments are especially useful in thermal leak detection in higher temperature pneumatic ducting systems, from about 200 degrees F. to about 500 degrees F., and greatly reduce aircraft maintainer exposure risk in this temperature range.

For well over 30 years, there has been no viable support equipment to detect pneumatic leaks in the ECS of F/A-18 aircraft and their progeny. Existing leak devices have been widely disregarded by the fleet due to awkwardness and inability to produce readings without false positives. As a result, the currently utilized method to detect hot air leaks within the bleed air subsystem of the F/A-18 ECS is to use one's hands to check for airflow.

Many environments are high turbulence areas, which can adversely affect readings. In particular, aircraft engine bays are highly turbulent during engine operation. Additionally, in aircraft environments, particularly in the engine bays, the tested areas are very tight, confined areas. During the significant testing of the embodiments, maneuverability in those spaces was readily important, making the ability to have something shaped or configurable to a certain shape beneficial.

Embodiments offer a safe approach to determining the leakage location as well as the temperature and severity of the airflow. Aircraft maintainers can use the embodiments to distinguish this from a safe distance with a stainless steel probe, sometimes referred to as a shaft and measurement head. During use, the measurement head is near hot ducting. Stainless steel is used for the shaft and measurement head to slow heat transfer to the handle, thereby protecting the user. Additionally, stainless steel is better in high temperature environments compared to other metals. The probe is equipped with a plurality thermocouples wired in parallel to detect an average temperature over all of the sensors. This allows the user a larger scan area when searching for leaks with the probe.

Although embodiments are described in considerable detail, including references to certain versions thereof, other versions are possible. Examples of other versions include alternative configurations allowing for operating safety without sacrificing accuracy. Therefore, the spirit and scope of the appended claims should not be limited to the description of versions included herein.

In the accompanying drawings, like reference numbers indicate like elements. FIG. 1 illustrates an apparatus, according to some embodiments. Reference character 100 depicts an apparatus of embodiments. Components may exist singularly or in pluralities, even though depicted as one or the other in the figures for simplified viewing, without detracting from the merits or generality of embodiments.

Figure 4:
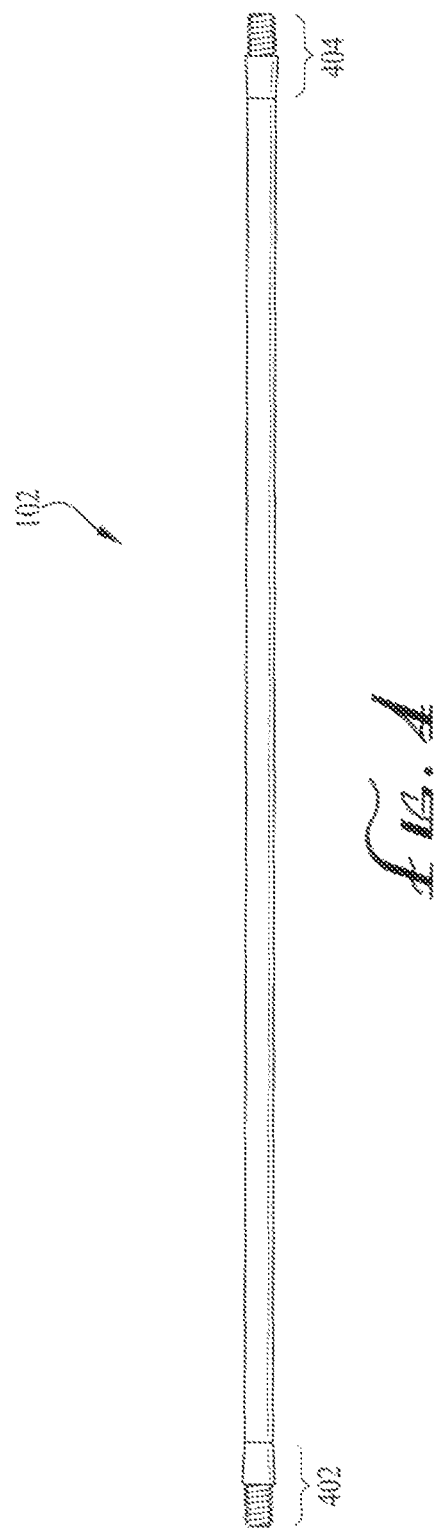
FIG. 4 is a side view of a shaft portion of the apparatus in FIG. 1.

Referring to FIG. 1, embodiments generally relate to a thermal leak detector 100 used in pneumatic systems. The thermal leak detector 100 is sometimes referred to as the apparatus, device, or detector, or thermal leak detection device. As such, the terms are used interchangeably. The device 100 includes a hollow probe 102, sometimes referred to as a shaft, having a proximal end 402 (FIG. 4) and a distal end 404 (FIG. 4). A hollow insulated handle 104 is attached to the proximal end 402 of the hollow probe 102. A measurement head 106 is attached to the distal end 404 of the hollow probe 102. An electronic thermometer 108 is electrically-connected to the measurement 106. As will be apparent when viewing the figures, the hollow probe 102 and hollow insulated handle 104 are a conduit for a wire bundle 110 from the measurement head 106 to the electronic thermometer 108.

The hollow probe 102 is a semi-rigid, flexible rod, sometimes referred to as a semi-flexible shaft configured to change and maintain geometric shape upon manual actuation by a user. The hollow probe 102 is sometimes described as being configurable, geometrically-configurable, and semi-geometrically configurable. The corresponding shape is configurable by a user and is governed by the particular operating environment and the particular component, such as ducting, flange, or pipe, that is being tested, sometimes referred to as the component being acted upon.

Figure 5:
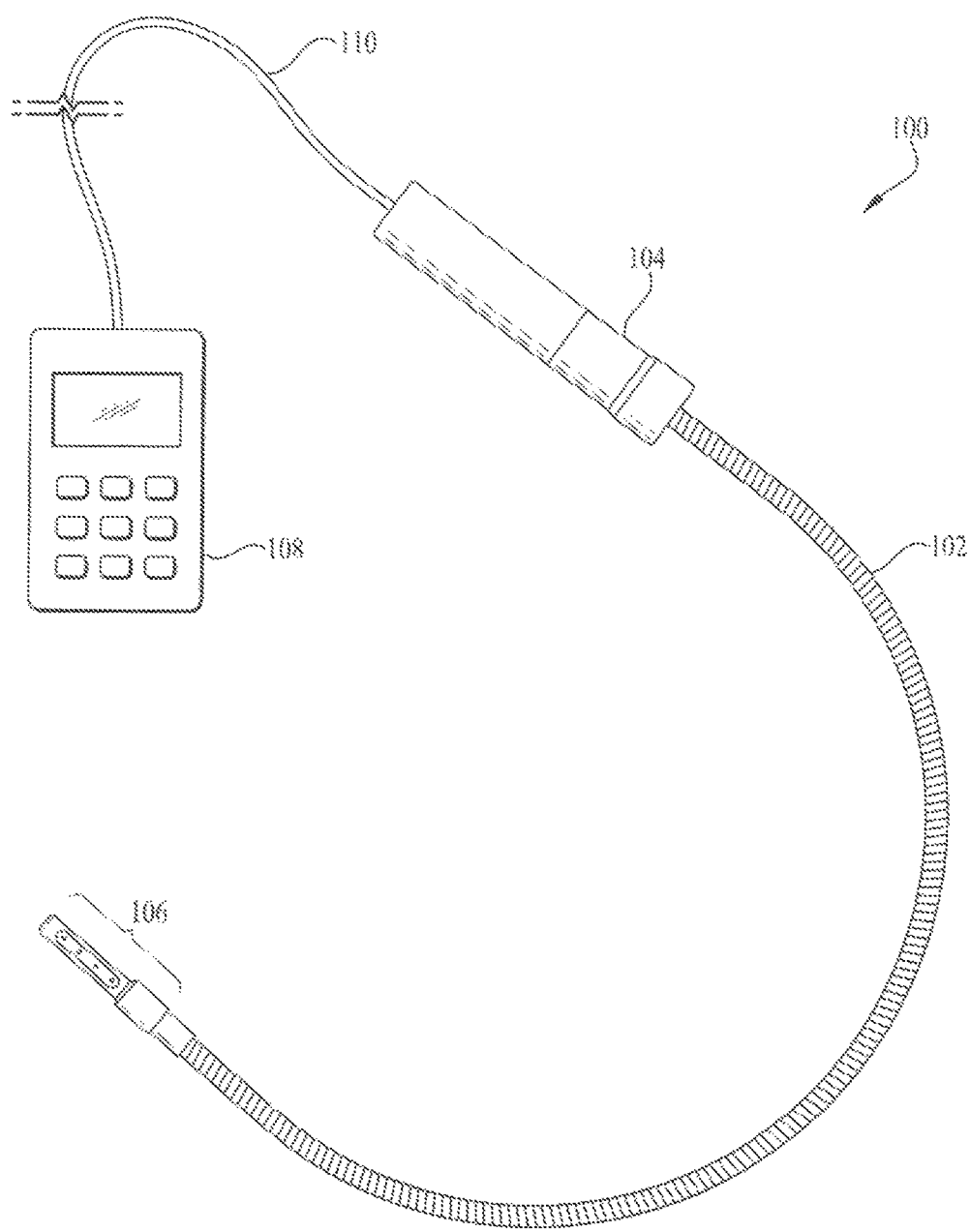
FIG. 5 is a plan view of a thermal leak detector, according to some embodiments, including the apparatus (FIG. 1) shown with the shaft in a user-actuated gooseneck shape, the measurement head (FIG. 2A), the thermocouple plate and thermocouples (FIGS. 3A, 3B, & 3C), a handle attached to the distal end of the shaft portion (FIG. 4), and a digital thermometer electrically-connected through the handle, the shaft portion, and the measurement head, underneath the thermocouple plate (FIGS. 3A & 3B), and to the thermocouples (FIGS. 3C & 6).

The device 100, and particularly the hollow shaft 102, is configured to maintain its shape when shaped by the user. The semi-flexible shaft 102 is shown in an actuated position in FIG. 5. The shape can be considered an arc, arcuate, or gooseneck shape because of the curvature of the shaft 102. The shaft 102 is configurable by a user and is able to maintain its shape until external forces are applied to the shaft to change its shape. Referring to both FIGS. 1 & 5, it is apparent that the device 100 is configurable to a variety of positions. In particular, FIG. 1 can be considered as depicting a first position of the device 100 and FIG. 5 can be considered as depicting a second position of the device. The configurable nature of the shaft 102 is depicted in FIG. 5 (the gooseneck orientation) as segmented, sometimes referred to as stainless steel flexible guide tube. The remaining figures do not show segments for ease of viewing.

The shaft 102 in FIG. 5 can also be considered as a sigmoid, ogee, and cyma recta shape. A person having ordinary skill in the art will recognize that ogee and cyma recta are understood to be types of sigmoid shapes. A person having ordinary skill in the art will recognize that a sigmoid shape is a shape similar to the letter S. Likewise, a person having ordinary skill in the art will recognize that an ogee shape is descriptive of an S-shape and, moreover, is characteristic of two curves meeting at a point. Additionally, a person having ordinary skill in the art will recognize that a cyma *recta* shape is descriptive of double curvature, combining both convex and concave features.

FIGS. 2A, 2B, & 2C depict different views of the measurement head 106. The measurement head 106 is a hollow stainless steel housing having a first portion 201 and a second portion 203. The housing 106 has an outer surface 202, an inner surface 204, and is centered about a common longitudinal axis 206. The inner surface 204 of the first portion 201 is threaded to match threads on the distal end 404 of the hollow shaft 102. The inner surface's 204 threading in the first portion 201 is not shown for ease of view. The inner surface 204 of the second portion 203 is not threaded. Similarly, the inner surface (not shown) of the hollow handle 104 is threaded to match the threads on the proximal end 402 of the hollow shaft 102.

It is apparent from viewing FIGS. 1, 2A, 2B, 2C, and 4, that the first portion 201 of the housing 106 is configured to threadingly-engage with the distal end 404 of the hollow shaft 102. Likewise, it is also apparent from the figures that the threading on the inner surface of the hollow handle 104 is configured to threadingly-engage with the proximal end 402 of the hollow shaft 102.

The housing 106 has a stair-stepped recess 208 in at least one portion of the housing. As shown in FIGS. 2B & 2C, the stair-stepped recess 208 is in the second portion 203 of the housing 106. Each step in the stair-stepped recess 208 corresponds to an increasing depth inward, perpendicular to the common longitudinal axis 206, as measured inward from the outer surface 202.

FIGS. 3A, 3B, & 3C depict a plate 300. The plate 300 can be referred to as a thermocouple plate because it is configured to fixedly-hold thermocouples. The plate 300 is insulated. In some embodiments, the plate 300 is an insulated aluminum plate. In other embodiments, the plate 300 is an anodized aluminum plate. The plate 300 has an upper surface 302 and a lower surface 304. The plate 300 is dimensioned to fit in the stair-stepped recess 208. The lower surface 304 of the plate 300 is attached to the first step 210 in the stair-stepped recess 208. The attachment is by epoxy or glue.

A plurality of voids 306, depicted as apertures or holes, are longitudinally-aligned parallel with the common longitudinal axis 206. A plurality of thermocouples 310, equal in number to the plurality of voids 306, is used for thermal sensing. Each thermocouple in the plurality of thermocouples 310 has a corresponding void in the plurality of voids 306, with each of the thermocouples affixed in the corresponding voids. The affixation is by bonding or glue.

Figure 6:
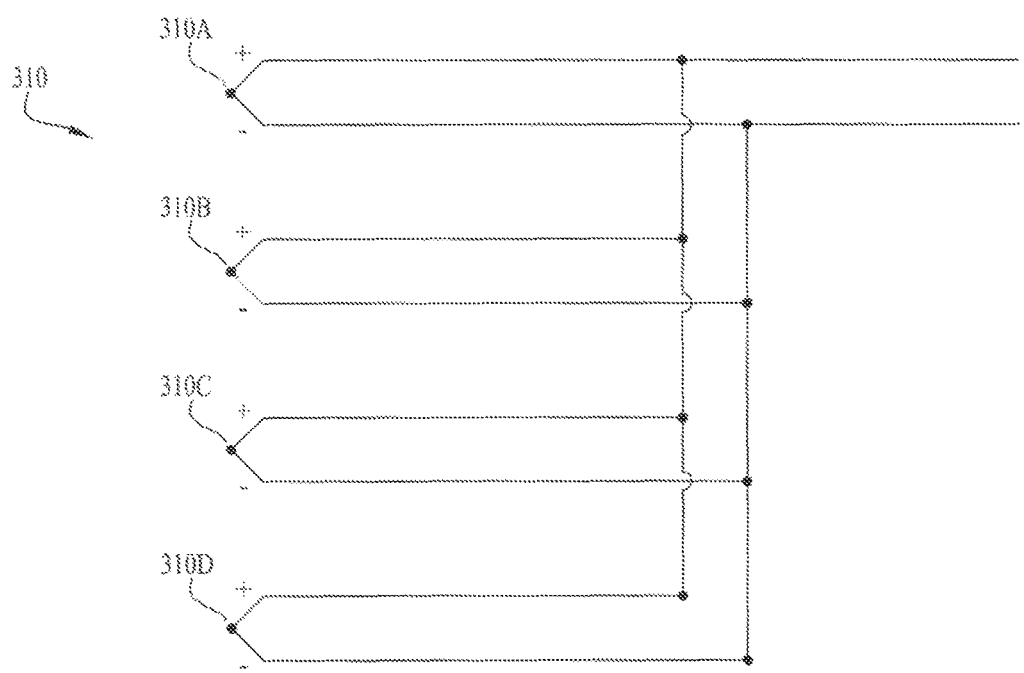
FIG. 6 is an exemplary schematic depicting a plurality of thermocouples connected in parallel, according to the embodiments.

Referring to FIG. 6, the plurality of thermocouples 310 are wired in parallel with each other, and is electrically-connected in the wire bundle 110 to the electronic thermometer 108. Four thermocouples 310A, 310B, 310C, and 310D are shown in FIG. 6. The first thermocouple 310A is physically closer to the electronic thermometer 108 than the other thermocouples 310B, 310C, & 3100. The fourth thermocouple 310D is farthest from the electronic thermometer 108.

The number of thermocouples in the plurality of thermocouples 310 is a range of about three to about five thermocouples. In some embodiments the number of thermocouples 310 is four. In the embodiments, the way that the thermocouples 310 are nested in the thermocouple plate 300 permits leaking air to pass into and through the probe, via the stair-stepped recess 208 and warm up the thermocouples, therefore allowing the average to more accurately represent the temperature of leak. This configuration provides sensitivity to high temperature, high pressure flows escaping from the ducts and flanges in the presence of a leak. Embodiments have undergone significant testing and accurately detect a leakage rate of 0.009 pounds per minute, corresponding to a calculated volumetric flow rate of 3.375 cubic feet per hour.

The thermocouples 310 arrangement in the measurement head 106 protect the thermocouple junctions. If aircraft maintainers accidently cause the measurement head 106 to make inadvertent contact with a flange, the readings will not be affected because the thermocouples 310 are not directly exposed to the flange.

During the testing, the plurality of thermocouples 310 used were K-type thermocouples. A person having ordinary skill in the art will recognize that K-type thermocouples offer an extremely wide temperature range (−270 C to 1372 C and −454 F to 2501 F). The positive lead for each K-type thermocouple is chrome nickel-chromium (Ni—Cr) and the negative lead is nickel-aluminum (Ni—Al). Embodiments can also use other types of thermocouples capable of performing in the temperature range for leak detection (from about 20 degrees F. to about 500 degrees F.) discussed herein. The additional thermocouple types include J-type thermocouples, T-type thermocouples, E-type thermocouples, and N-type thermocouples.

The wire bundle 110 is insulated and is sometimes referred to as an insulated electrical bundle, electrical bundle, or bundle. The wire bundle 110 routes the parallel wiring of the plurality of thermocouples 310 from and through the measurement head 106, through the distal end 404 of the hollow shaft 102, down the entire length of the hollow shaft, through the proximal end 402 of the hollow shaft, through the hollow insulated handle 104, and finally to the electronic thermometer 108.

The hollow insulated handle 104 is configured to fit a user's hand. Due to the close quarters that the apparatus 100 is used in, the hollow shaft 102 is less than thirteen inches long, measured from proximal end 402 to distal end 404. The measurement head 106 is about two inches long. The hollow probe/hollow shaft 102 is a flexible, semi-configurable stainless steel shaft. The handle 104 can be aluminum or acrylonitrile butadiene styrene (ABS). However, the concepts employed as disclosed herein are applicable to varying lengths, without detracting from the merits or generalities of the various embodiments. In the embodiments, the electronic thermometer 108 is a digital thermometer. The digital thermometer 108 has a visual display screen and is configured to display temperature/temperature differences (temperature delta) corresponding to leaks in pneumatic piping systems.

Embodiments can be used in numerous pneumatic ducting systems and environments. FIGS. 7A & 7B illustrate a portion of the ducting and coupling that embodiments are configured to act upon. FIG. 7A displays a testing environment 700, which can be considered as a ducting under test, including a wye duct 702. The wye duct 702 is used in aircraft pneumatic bleed systems in aircraft engine bays. FIG. 7B shows coupling system 704 including an open (unactuated) V-band clamp 706 with E-seal 708 that is used with the wye duct 702 in FIG. 7A. The E-seal 708 is a high temperature, high pressure formed metal gasket that, when placed between two tightened mating surfaces, will crush and form a seal within the flanges.

The coupling system 704 and wye duct 702 combination can be referred to as a flange. The coupling system 704 is shown with the V-band clamp 706 closed in FIG. 7A in three locations of the wye duct 702. In aircraft environments, flanges in the bleed air sections contain V-band clamps 706 and E-seals 708 that are coupled together and around the ends of the wye ducts 702. The V-band clamps 706 and E-seals 708 are constructed to withstand high pressures, flow rates, and temperatures. In general, maximum allowable leak rates at flanges is 0.003 lbs/min/inch according to specific V-band clamp requirements. For three inch diameter ducting, the allowable leakage rate is set at 0.009 lbs/min. For two inch diameter ducting, the allowable leakage rate is 0.006 lbs/min.

Thermocouples operate on the basis of the thermoelectric effect. A change in temperature sensed at the tip of a thermocouple will directly change the voltage that it will apply to the digital thermometer 108. When wired in parallel, readings are averaged over a predetermined distance across all of the thermocouple tips. In some embodiments, different attachment measurement heads 106 are configured to wrap around the flanges and detect small leaks in any direction, permitting a broader scan radius. In other embodiments, the semi-flexible shaft 102 is configured to change geometric shape upon actuation by a user. The change in geometric shape allows the user to configure the apparatus 100 to a desired orientation, allowing the user to articulate the probe to and around a desired temperature measurement location, such as the wye duct 702 located in an aircraft bleed system. Multiple thermocouples 310 wired in parallel provide a broader scan radius which is better than a single thermocouple because it does not require the operator to manipulate a single thermocouple around a potential leak site.

In embodiments, the semi-flexible probe orientation resembles a gooseneck. The apparatus 100 is handheld, which is more useful in confined and austere environments. In general, voids 306 in the thermocouple plate 300 are spaced at about one-quarter inch apart from each other and in a straight line longitudinally. Likewise, the thermocouples 310 are spaced about one-quarter inch apart from each other. In some embodiments, the number of voids 306 is a range of three to five, depending on application-specific conditions. In other embodiments, the number of voids 306 is four. The thermocouples 310 are wired in parallel with each other and then terminate in the wire bundle 110, which is hardwired into the digital thermometer 108. Material selection is due, in part, due to the apparatus 100 being used in maritime and other humid environments. As such, stainless is used in several components are noted herein.

In application, embodiments are used to detect in leaks in pneumatic systems by determining temperature difference or change, sometimes referred to as a temperature delta. Depending on where the aircraft is physically located such as, for example, a particular building, a particular location in the world, engine bay temperatures will be different. There is no standardized temperature. The temperatures will depend on how the aircraft engine is running. Likewise, the bay temperatures increase as the engine runs.

When the apparatus 100 configured with the thermocouples 310, is scanned over a duct and temperatures sampled from a duct that is not leaking, the temperature reading is the engine bay temperature. However, once a leak is found, then the delta of the leak coming from the duct will show as a temperature spike. In general, the engine bay temperature will be from about 100 degrees F. to about 200 degrees F. during normal operating conditions (from cold to hot as the aircraft engine runs).

When the temperature goes above 200 degrees F., then either a thermocouple 310 has actually touched the metal ducting or the apparatus 100, specifically the measurement head 106, is in the leak path and the leak has been located. Embodiments buffer the thermocouples 310 from the object (ducting) being tested because the thermocouples 310, as shown in FIG. 3B, do not extend past the upper surface 302 of the plate 300. Likewise, when the plate 300 is affixed to the first step 210 in the stair-stepped recess 208, the upper surface 302 of the plate 300 is inside the housing 106 and does not extend to or past the outer surface 202 of the housing. This prevents the thermocouples 310 from touching ducting, such as hot metal, which prevents false positive readings.

As such, when the embodiments exhibit a temperature increase greater than 200 degrees F., the measurement head 106 is in the leak path and the leak is located. Furthermore, during significant testing, the apparatus 100 detected leaks having temperature differences as small as 30 degrees F. Likewise, the apparatus 100 performed admirably in detecting cold air leaks.

While the embodiments have been described, disclosed, illustrated and shown in various terms of certain embodiments or modifications which it has presumed in practice, the scope of the embodiments is not intended to be, nor should it be deemed to be, limited thereby and such other modifications or embodiments as may be suggested by the teachings herein are particularly reserved especially as they fall within the breadth and scope of the claims here appended.

What is claimed is:

1. A thermal leak detection device, comprising:
   a hollow probe having a proximal end and a distal end;
   a hollow insulated handle attached to said proximal end of said hollow probe;
   a measurement head attached to said distal end of said hollow probe; and
   an electronic thermometer electrically-connected to said measurement head;
   wherein said measurement head, further comprising:
     a hollow stainless steel housing having an outer surface, an inner surface, and centered about a common longitudinal axis;
     a stair-stepped recess in at least one portion of said housing, wherein each step in said stair-stepped recess corresponding to an increasing depth inward as measured from said outer surface;
     a plate having an upper surface and a lower surface, said plate dimensioned to fit in said stair-stepped recess, wherein said lower surface of said plate is attached to the first step in said stair-stepped recess;
     a plurality of voids in said plate, wherein said plurality of voids are longitudinally aligned parallel with said common longitudinal axis; and
     a plurality of thermocouples equal in number to said plurality of voids in said plate, wherein each thermocouple in said plurality of thermocouples having a corresponding void in said plurality of voids, wherein each of said thermocouple is affixed in said corresponding void;
   wherein said plurality of thermocouples are wired in parallel and electrically-connected to said electronic thermometer.

2. The device according to claim 1, wherein said hollow probe is a geometrically, shape-configurable rod configured to change geometric shape upon manual actuation by a user.

3. The device according to claim 1, wherein said electrical connection, further comprising an insulated electrical bundle corresponding to said parallel wiring of said plurality of thermocouples, said electrical bundle routed through stainless steel housing of said measurement head, through said distal end of said hollow probe, through said hollow probe, through said proximal end of said hollow probe, through said hollow insulated handle, and to said electronic thermometer.

4. The device according to claim 1, wherein said plurality of thermocouples are a range of about three to about five thermocouples.

5. The device according to claim 1, wherein said plurality of thermocouples is four thermocouples.

6. The device according to claim 1, wherein said hollow insulated handle is configured to fit in a user's hand.

7. The device according to claim 1, wherein said electronic thermometer is a digital thermometer.

* * * * *